(12) United States Patent
Yoshida

(10) Patent No.: US 6,841,709 B2
(45) Date of Patent: Jan. 11, 2005

(54) METHOD OF CUTTING POLYMER CHAINS AND METHOD FOR PRODUCING CHEMICAL RAW MATERIALS

(76) Inventor: Masaaki Yoshida, 2-4-20, Izumigaka, Utsunomiya-Shi, Tochigi, 321-0952 (JP)

( * ) Notice: Subject to any disclaimer, the term of this patent is extended or adjusted under 35 U.S.C. 154(b) by 73 days.

(21) Appl. No.: 09/984,519

(22) Filed: Oct. 30, 2001

(65) Prior Publication Data

US 2002/0103301 A1 Aug. 1, 2002

(30) Foreign Application Priority Data

Oct. 31, 2000 (JP) ......................................... 2000-332693

(51) Int. Cl.[7] .............................. C10G 1/10; C10G 1/00; C07C 4/00; C07C 55/00
(52) U.S. Cl. ........................ 585/241; 585/240; 585/324; 585/613; 585/648; 585/242; 540/540; 540/538; 540/485; 549/427; 252/182.12; 252/162.12; 562/590
(58) Field of Search ................................. 585/241, 240, 585/324, 613, 648, 242; 540/540, 538, 485; 549/427; 252/182.12, 162.12; 562/590

(56) References Cited

PUBLICATIONS

Remias, J.E., Pavlosky, T.A., & Sen, A., "Oxidative Chemical Recycling of Polyethylene" pp. 627–629, *C.R. Acad. Sci. Paris*, Ser. IIc, Chem., 3; 2000.

*Primary Examiner*—Johann Richter
*Assistant Examiner*—Elvis O. Price
(74) *Attorney, Agent, or Firm*—Duane Morris LLP

(57) ABSTRACT

The present invention is to provide a technology to establish a new cycle-based organic chemical industry, which may be called a polymer cascade (polymer reflux industry) wherein the polymer substances shall not remain the final products, but still give birth to synthetic materials as raw materials for chemical industry and produce useful organic compounds.

The present invention to destroy polymer substances by severing a part of molecular chains from the said polymer substances by means of allowing nitrogen dioxide and/or dinitrogen tetraoxide to do oxidative decomposition reaction in inert gas, or destroying polymer substances by severing a part or all of molecular chains from the said polymer substances by allowing nitrogen dioxide and/or dinitrogen tetraoxide to do oxidative decomposition reaction in supercritical carbon dioxide, or to treat polymer substances that are at least one of what are selected from polymer substances of addition polymerization type, polyaddition type, polycondensation type or addition condensation type, or waste polymers thereof, or petroleum fraction of high boiling point.

10 Claims, No Drawings

METHOD OF CUTTING POLYMER CHAINS AND METHOD FOR PRODUCING CHEMICAL RAW MATERIALS

BACKGROUND OF THE PRESENT INVENTION

1. Field of the Invention

The present invention relates to a technology providing a destructive program for synthetic polymers, which are man-made.

2. Description of the Related Art

Creatures unceasingly produce in their cells various kind of high molecular compounds including DNA, proteins and saccharide. However, the thus produced high molecular compounds are destroyed and metabolized after duly utilized. In other words, every creature is provided with what is called a destructive program, and such mechanism maintains the life of creatures. Cancer cells, different from all other ones, are lacking in such destructive program. The Earth being assumed as a complex of lives, synthetic polymer compounds may be compared to the Earth's cancer cells, which have no destructive program.

Therefore, the inventor considers that it will be extremely important in contributing to the sustainable development of human beings in the 21st Century to provide a program destructive of the synthetic polymers, which human beings have been creating.

The destructive program envisaged by the inventor of the present invention is not related to incineration or pyrolysis, but to the cutting of molecular chains by means of chemical reaction as seen in regard to creatures wherein it is possible reusable compounds of high value-added, depending on the extent of cutting.

Conventional methods for recycling polymers include the 'thermal recycling' that is designed to utilize heat generated through incineration of polymers, the 'material recycling' that is designed to mold anew waste polymers into some usable articles and the 'chemical recycling' that is designed to convert waste polymers into monomers or other chemicals. The 'material recycling' is devoted to metamorphosing polymers in repetitive manners still ending up with leaving wastes behind, which cannot be the solution of waste polymer treatment issues.

SUMMARY OF THE INVENTION

In today's petrochemical industry, lower olefins, aromatic hydrocarbons such as BTX, and synthetic gases serve as raw materials, and those small molecules are linked into forming organic compound products. Among those products the largest amount in production are accounted for by polymer substances, which consist of a very long linkage of small-size molecules, constitute the final form of synthesis and have so far been wasted after utilized.

The inventor of the present invention considers that it is one of the most important themes in the world to establish a new cycle-based organic chemical industry, which may be called a polymer, cascade (polymer reflux industry) wherein the polymer substances shall not remain the final products, but still serve as raw materials for producing useful organic compounds.

In order to utilize the polymer substances as raw materials it is necessary to have a means to cut high molecular chains thereof to any manner and extent as desired. It is as if there is a need of having a saw to cut timbers or plates for making woodworks, or scissors to cut cloths for making clothes.

In recent years, research has been conducted on 'chemical recycling' as a means to treat waste polymers, however, it has been focusing only on the technologies of monomerization or liquefaction, which both require thermal energy.

In particular, addition polymerization-type polymer substances such as polyethylene and polypropylene are regarded as valueless as raw materials for chemical industry owing to lack in reactivity due to their chemical stableness, and they are not considered as usable for any other purpose than fuel or material recycling.

However, given that most of polymer substances produced in the world are of addition polymerization type, the inventor of the present invention thinks it to be the mission of the chemical industry in the cycle-based society to develop a technology that would facilitate such polymer substances to react.

Therefore, it is the object of the present invention to provide a technology to build a new cycle-based organic chemical industry, which may be called a polymer cascade (polymer reflux industry), wherein the polymer substances should not remain the final products, but shall still serve as raw materials for producing useful organic compounds.

Another object of the present invention is to provide a technology to obtain chemical compounds of high value-added by means of oxidative decomposition of the polymer substances and the wastes thereof and the like under a relatively moderate condition for the purpose of making the polymer substances harmonious with the cycle-based society in the 21st Century.

Other and further objects of the present invention will be clarified in the following descriptions.

The inventor of the present invention, in an intensive effort to achieve the aforementioned objects, has reached the present invention as a consequence of finding that dicarboxylic acid group, etc. of high value-added are selectively obtainable, as oxidative decomposition occurs under a relatively moderate condition when the polymer substances are made to react by means of nitrogen dioxide or nitrogen tetraoxide in inert gas, or particularly in supercritical carbon dioxide.

DESCRIPTION OF THE INVENTION AND PREFERRED EMBODIMENTS

Method for Cutting Polymer Chains

The polymer substances subject to cut in the present invention include addition polymerization-type polymer substances such as polyethylene, polypropylene, polystyrene, polyvinyl chloride, polyvinyl acetate, polyvinyl alcohol, methacrylic acid resin, fluororesin, polyacrylonitrile, butadiene rubber, isoprene rubber, chloroprene rubber, polyacetylene, polyphenylene, polypyrrole, polythiophene, polyacetal resin and allyl resin, and polyaddition-type polymer substances such as polyurethane and epoxy resin, and polycondensation-type polymer substances such as polyamide, polyester, polycarbonate, polyphenylene oxide, and addition condensation-type polymer substances such as phenol resin, urea resin, melamine resin, and in addition, may include either co-polymers of two or more thereof, or mixtures thereof, and further may be those cross-linked, if the main molecular chain is of carbon-to-carbon bond, or those having functional groups.

Furthermore, the polymer substances related to the present invention may also include waste polymers of the said polymer substances, high boiling fraction of petroleum and even coal.

The method for cutting the polymer substances in the present prevention is cutting a part or all of the molecular chains of polymer substances by nitrogen oxide in inert gas.

Inert gas, as used in the present invention may be, but not limited to, carbon dioxide, nitrogen, argon and helium, among which carbon dioxide is preferable, and supercritical carbon dioxide is more preferable.

In the nitrogen oxide, as used in the present invention are included nitrogen dioxide, dinitrogen tetraoxide, nitrogen monoxide, dinitrogen monoxide and dinitrogen trioxide, each of which can be used either solely or in combination, and among which nitrogen dioxide and/or dinitrogen tetraoxide is preferable.

The reasons why the reaction by means of nitrogen dioxide and/or dinitrogen tetraoxide in supercritical carbon dioxide is preferable are recounted as follows:

The reaction of dinitrogen tetraoxide cleaving into 2 molecules of nitrogen dioxide ($N_2O_4=2NO_2$) is equilibrium reaction. When the dinitrogen tetraoxide cleaves, nitrogen dioxide radicals are generated. These nitrogen dioxide radicals are quite reactive, however the reaction thereof is strongly inhibited in supercritical carbon dioxide owing to what is called a radical cage, or besiegement by carbon dioxide molecules. When plastics are oxidized by nitrogen dioxide as an oxidizing agent in supercritical carbon dioxide, nitrogen dioxide radicals enter in a radical cage and are restrained from their reactiveness, and at the same time thanks to the highly permeative and highly diffusive characteristics of the supercritical fluid carried deeply into the molecular chains of the plastics wherein relieved of the protection of the carbon dioxide, they actively and efficiently do oxidative reaction. Hence, oxidative reaction of substances such as solid plastics by means of nitrogen dioxide in supercritical carbon dioxide is the reaction system wherein violent reaction is inhibited, and, at the same time, efficient reaction is promoted.

The present invention is designed to provide the program destructive of synthetic polymer, which human beings have been creating, and to thereby contribute to the sustainable development of human beings in the 21st Century.

The destructive program in the present invention, different from incineration or pyrolysis, is designed to cut molecular chains by means of chemical reaction as is done by creatures wherein it is possible not only to attain a thorough decomposition but also to recover reusable compounds of high value-added, depending on the extent of cutting.

Namely, the present invention is designed to provide the technology to establish a new cycle-based organic chemical industry, which may be called a polymer cascade (polymer reflux industry) wherein the polymer substances shall not remain standing as the final products, but still serve as raw materials to produce synthetic materials and useful organic compounds.

In the present invention the chemical compounds obtained by means of destroying the polymer substances include even those medium-size or small-size molecules severed from the molecular chains of the polymers from the standpoint of building a new cycle-based organic chemical industry, which may be called a polymer cascade (polymer reflux industry) wherein the polymer substances shall serve as raw materials for industry to produce synthetic materials and useful organic compounds.

For the purpose of the present invention the "medium-size molecules" mean those having a fracture rate (FR) of more than 0% but no more than 80% ($0\%<FR\leq80\%$), when the large polymer substances are destroyed according to the method in the present invention, and the "small-size molecules," mean those having FR of more than 80% but no more than 100% ($80\%<FR\leq100\%$), when the large polymer substances are destroyed according to the method in the present invention and those obtained from destruction of the said medium-size molecules and having a fracture rate (FR2) of no less than 20% but no more than 100%. Therefore, as used in the present convention, the concept of medium-size and small-size molecules shall not be defined according to molecular weight, but shall be so defined as to include those molecules that are made lower in molecular weight at any rate than their prescriptions according to the method of destruction in the present invention and also to include those having only one carbon chain after fully decomposed (in case decomposed into carbon dioxide and water, etc).

The thus obtained small-size and medium-size molecules have a variety of uses as compound materials or products. Those polymer substances rid of the molecular chains thereof as well as those severed from the said polymer substances are functionalized at the severance points thereof, resulting in having different characteristics from the original polymer substances with the potential of new uses as well as resulting in the possible reforming of the original substances through reaction by means of the functional group.

As concerns the method for destroying the polymer substances in the present invention, it is preferable to control the molecular chain length by means of ① changing the quantities of nitrogen oxide in relation to those of the said polymer substances, ② changing reaction temperature, ③ changing reaction pressure by means of inert gas, ④ changing reaction time, and ⑤ changing additives.

The means of controlling the molecular chain length as enumerated above can be described more in detail as follows:

Firstly, in case of changing the quantities of nitrogen oxide in relation to those of the said polymer, as mentioned in ① above, a tight attack of the nitrogen oxide on the carbon chains makes the carbon chains of the product short, and a loose attack makes the carbon chains of the product long, therefore products having any range of carbon chain length whatever can be obtained by controlling the quantities of the nitrogen oxide.

Secondly, in case of changing reaction temperature, as mentioned in ② above, the temperature of oxidative decomposition is preferably lower than that of pyrolysis or depolymerization of the said polymer substances, which is not only energy-saving, but also prevents the products from growing too small, as is the case when the temperature is high, leading to the possible detriment of the value-added of the products. The low temperature does not only make the carbon chains of the products long, but also make it possible to obtain highly oxidative reaction intermediates.

Thirdly, in case of changing reaction pressure by means of inert gas, as mentioned in ③ above, the change of reaction pressure by means of inert gas makes it possible to control the balance between nitrogen dioxide and dinitrogen tetraoxide, and inhibit an explosive radical reaction and instead, promote a modest reaction. Besides, the control thereby of the degree of oxidative reaction activity makes it possible to obtain the products having any length of carbon chains whatever.

Fourthly, in case of changing reaction time, as mentioned in ④ above, the fact that oxidation proceeds, as time goes on makes it possible to control the length of the carbon chains of the products according to the length of the reaction.

Fifthly, in case of changing additives, as mentioned in ⑤ above, addition of catalysts such as metal oxides or additives such as organic compounds makes it possible to accelerate or decelerate reaction to control the length of the carbon chains of the products.

In the present invention the chemical compounds represented by the following general formula [1], [2], [3], [4], [5], [6] or [7] can be obtained by means of the aforementioned method for destroying the polymer substances:

The general formula [1]: HOOCRCOOH
The general formula [2]: HOOCRNO$_2$
The general formula [3]: HOOCRNO
The general formula [4]: ONRNO
The general formula [5]: ONRNO$_2$
The general formula [6]: O$_2$NRNO$_2$ R appearing in the above formulae represents zero, one or more carbon chains, which may or may not have branching, may or may not be cyclized, and in addition may have a unsaturated linkage. Furthermore, the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group. The said substituents may further be replaced by other ones.

The general formula [7]: RCOOH

R appearing in the above formula represents the hydrogen atoms, one or more carbon chains, which may or may not have branching, may or may not be cyclized, and in addition may have a unsaturated linkage.

Furthermore, the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group. The said substituents may further be replaced by other ones.

Concrete examples of the chemical compounds represented by the above general formula [1], [2], [3], [4], [5], [6] or [7] include, but are not limited to, succinic acid, glutaric acid, adipic acid, sebacic acid, pimelic acid, suberic acid, methyl succinic acid, 2,4-dimethyl glutaric acid, benzoic acid, 4-nitrobenzoic acid and terephthalic acid.

Method for Producing Chemical Raw Materials

The method for producing chemical raw materials in relation to the present invention is intended to obtain chemicals usable as chemical raw materials comprising medium-size molecules or small-size molecules through cutting a part or all of the molecular chains of the polymer substances by means of oxidative decomposition reaction, using nitrogen oxide in inert gas.

For the purpose of the present invention medium-size molecules or small-size molecules are as defined in the preceding article for the method for destroying the polymer substances.

A preferable embodiment of the method for producing chemical raw materials is to cut a part or all of the molecular chains in the polymer substances by making them react to obtain chemicals usable as chemical raw materials comprising medium-size molecules or small-size molecules through cutting a part or all of the molecular chains of the polymer substances by means of oxidative decomposition reaction in supercritical nitrogen dioxide.

The polymer substances to be used as raw material may be the same as those enumerated in the preceding article of the method for destroying the polymer substances.

The means of controlling the length of the molecular chains of the polymer substances may also be the same as described in the said preceding article.

The chemical compounds obtained according to the method for producing chemical raw materials in the present invention include, but are not limited to, those represented by the aforesaid formula [1], [2], [3], [4], [5], [6] or [7], which constitute the chemicals usable as chemical raw materials comprising medium-size molecules or small-size molecules.

The present invention makes it possible to realize a new cycle-based organic chemical industry, which may be called a polymer cascade (polymer reflux industry) wherein the polymer substances shall still serve as raw materials comprising medium-size molecules or small-size molecules to produce synthetic materials and useful organic compounds.

As described in the preceding article of the method for destroying polymer substances, medium-size molecules or small-size molecules have a variety of uses as compound materials or products. Those medium-size molecules or small-size molecules as well as the polymer substances rid of parts of their molecular chains are functionalized at the severance points thereof, resulting in having different characteristics from the original substances with the potential of new uses as well as resulting in the possible reforming of the original substances through reaction by means of the functional group.

EXAMPLES

The present invention will next be described in more detail by way of examples, which should not be construed as limiting the invention thereto.

Example 1

When 1.0 g of cross-linked low density polyethylene in the form of plate, 3.2 g of nitrogen dioxide and 16.3 g of liquefied carbon dioxide put in a 50 ml stainless steel autoclave were heated to 110° C., the pressure inside reached 9.0 MPa. After the mixture comprising the said substances was allowed to react at 110° C. for 15 hours, the autoclave was cooled until the pressure inside dropped back to atmospheric pressure, then opened to obtain 1.46 g of semisolid substance.

After methylesterified by diazomethane, this crude product was confirmed by means of gas chromatography with ethylbenzene as internal reference to contain 0.19 g of succinic acid, 0.20 g of glutaric acid, 0.16 g of adipic acid, 0.12 g of pimelic acid, 0.08 g of suberic acid, 0.04 g of azelaic acid and 0.02 g of sebacic acid. Besides, the average length of the chains of resulting dicarboxylic acid was estimated to be as length as 6.5 pieces of carbon by comparison of the $^1$H NMR areas of methyl proton and methylene proton of methyl esters with coumarin as internal standard.

Example 2

When 1.0 g of cross-linked low density polyethylene in the form of plate, 3.9 g of nitrogen dioxide and 17.6 g of liquefied carbon dioxide put in the 50 ml stainless steel autoclave were heated to 110° C., the pressure inside reached 12.1 MPa. After the mixture comprising the said substances was allowed to react at 110° C. for 15 hours, the autoclave was cooled until the pressure inside dropped back to atmospheric pressure, then opened to obtain 1.32 g of semisolid substance.

This crude product was confirmed by means of the said gas chromatography to contain 0.26 g of succinic acid, 0.24 g of glutaric acid, 0.16 g of adipic acid, 0.08 g of pimelic acid, 0.02 g of suberic acid, 0.01 g of azelaic acid and 0.01 g of sebacic acid. Besides, the average length of the chains of resulting dicarboxylic acid was estimated to be as length as 5.8 pieces of carbon with use of the said $^1$H NMR.

Example 3

When 1.0 g of cross-linked low density polyethylene in the form of plate, 2.5 g of nitrogen dioxide and 10.7 g of argon put in the 50 ml stainless steel autoclave were heated to 120° C., the pressure inside reached 13.3 MPa. After the mixture comprising the said substances was allowed to react at 120° C. for 1 hour, the autoclave was cooled until the pressure inside dropped back to atmospheric pressure, then opened to obtain 1.53 g of semisolid substance.

This crude product was confirmed by means of the said gas chromatography to contain 0.10 g of succinic acid, 0.12 g of glutaric acid, 0.10 g of adipic acid, 0.09 g of pimelic acid, 0.08 g of suberic acid, 0.06 g of azelaic acid and 0.05 g of sebacic acid. Besides, the average length of the chains of resulting dicarboxylic acid was estimated to be as length as 9.8 pieces of carbon with use of the said $^1$H NMR.

Example 4

When 1.0 g of low density polyethylene in the form of pellets, 3.2 g of nitrogen dioxide and 20.2 g of liquefied carbon dioxide put in the 50 ml stainless steel autoclave were heated to 130, the pressure inside reached 15.0 MPa. After the mixture comprising the said substances was allowed to react at 130° C. for 15 hours, the autoclave was cooled until the pressure inside dropped back to atmospheric pressure, then opened to obtained 1.27 g of semisolid substance.

This crude product was confirmed by means of the said gas chromatography to contain 0.26 g of succinic acid, 0.21 g of glutaric acid, 0.12 g of adipic acid, 0.05 g of pimelic acid, 0.01 g of suberic acid, 0.01 g of azelaic acid and 0.01 g of sebacic acid. Besides, the average length of the chains of resulting dicarboxylic acid was estimated to be as length as 5.7 pieces of carbon with use of the said $^1$H NMR.

Example 5

When 1.0 g of low density polyethylene in the form of pellets, 3.2 g of nitrogen dioxide and 19.8 g of liquefied carbon dioxide put in the 50 ml stainless steel autoclave were heated to 130° C., the pressure inside reached 15.0 MPa. After the mixture comprising the said substances was allowed to react at 130° C. for 4 hours, the autoclave was cooled until the pressure inside dropped back to atmospheric pressure, then opened. 1.66 g of semisolid substance were obtained therefrom.

This crude product was confirmed by means of the said gas chromatography to contain 0.10 g of succinic acid, 0.10 g of glutaric acid, 0.07 g of adipic acid, 0.05 g of pimelic acid, 0.03 g of suberic acid, 0.01 g of azelaic acid and 0.01 g of sebacic acid. Besides, the average length of the chains of resulting dicarboxylic acid was estimated to be as length as 8.1 pieces of carbon with use of the said $^1$H NMR.

Example 6

When 1.0 g of linear low density polyethylene in the form of pellets, 3.2 g of nitrogen dioxide and 17.8 g of liquefied carbon dioxide put in the 50 ml stainless steel autoclave were heated to 130° C., the pressure inside reached 14.4 MPa. After the mixture comprising the said substances was allowed to react at 130° C. for 15 hours, the autoclave was cooled until the pressure inside dropped back to atmospheric pressure, then opened. 1.24 g of semisolid substance were obtained therefrom.

This crude product was confirmed by means of the said gas chromatography to contain 0.18 g of succinic acid, 0.16 g of glutaric acid, 0.09 g of adipic acid, 0.04 g of pimelic acid, 0.01 g of suberic acid, 0.01 g of azelaic acid and 0.01 g of sebacic acid. Besides, the average length of the chains of resulting dicarboxylic acid was estimated to be as length as 6.1 pieces of carbon with use of the said $^1$H NMR.

Example 7

When 1.0 g of high density polyethylene in the form of pellets, 3.2 g of nitrogen dioxide and 19.2 g of liquefied carbon dioxide put in the 50 ml stainless steel autoclave were heated to 120° C., the pressure inside reached 13.9 MPa. After the mixture comprising the said substances was allowed to react at 120° C. for 15 hours, the autoclave was cooled until the pressure inside dropped back to atmospheric pressure, then opened. 1.46 g of semisolid substance were obtained therefrom.

This crude product was confirmed by means of the said gas chromatography to contain 0.25 g of succinic acid, 0.21 g of glutaric acid, 0.12 g of adipic acid, 0.06 g of pimelic acid, 0.01 g of suberic acid, 0.01 g of azelaic acid and 0.02 g of sebacic acid. Besides, the average length of the chains of resulting dicarboxylic acid was estimated to be as length as 6.5 pieces of with use of the said $^1$H NMR.

Example 8

When 1.0 g of high density polyethylene in the form of pellets, 3.2 g of nitrogen dioxide and 16.9 g of liquefied carbon dioxide put in the 50 ml stainless steel autoclave were heated to 130° C., the pressure inside reached 13.7 MPa. After the mixture comprising the said substances was allowed to react at 130° C. for 15 hours, the autoclave was cooled until the pressure inside dropped back to atmospheric pressure, then opened to obtain 1.32 g of semisolid substance.

This crude product was confirmed by means of the said gas chromatography to contain 0.25 g of succinic acid, 0.20 g of glutaric acid, 0.10 g of adipic acid, 0.04 g of pimelic acid, 0.01 g of suberic acid, 0.01 g of azelaic acid and 0.02 g of sebacic acid. Besides, the average length of the chains of resulting dicarboxylic acid was estimated to be as length as 5.5 pieces of carbon with use of the said $^1$H NMR.

Example 9

When, on the one hand, 0.2 g of high density polyethylene in the form of pellets, 3.1 g of nitrogen dioxide and 19.4 g of liquefied carbon dioxide put in the 50 ml stainless steel autoclave were heated to 130° C., the pressure inside reached 14.2 MPa. When, on the other hand, 0.2 g of high density polyethylene in the form of pellets, 3.1 g of nitrogen dioxide and 24.8 g of liquefied carbon dioxide were heated in the same manner to 130° C., the pressure inside reached 17.2 MPa. After each of the mixtures comprising the said substances was individually allowed to react at 130° C. for 1 hour, the autoclave was cooled until the pressure inside dropped back to atmospheric pressure, then opened to obtain 0.20 g and 0.18 g of semisolid substance, respectively. Besides, the average length of the chains of resulting dicarboxylic acid was estimated to be as length as 7.7 and 9.1 pieces of carbon respectively with use of the said $^1$H NMR.

Example 10

When 1.0 g of ultrahigh molecular weight polyethylene sample in powder form, 3.2 g of nitrogen dioxide and 21.1 g of liquefied carbon dioxide put in the 50 ml stainless steel autoclave were heated to 140° C., the pressure inside reached 17.4 MPa. After the mixture comprising the said substances was allowed to react at 140° C. for 15 hours, the autoclave was cooled until the pressure inside dropped back to atmospheric pressure, then opened to obtain 1.29 g of semisolid substance.

This crude product was confirmed by means of the said gas chromatography to contain 0.27 g of succinic acid, 0.20 g of glutaric acid, 0.09 g of adipic acid, 0.02 g of pimelic acid, 0.01 g of azelaic acid and 0.02 g of sebacic acid. Besides, the average length of the chains of resulting dicarboxylic acid was estimated to be as length as 5.9 pieces of carbon with use of the said $^1$H NMR.

Example 11

When 0.2 g of cross-linked low density polyethylene sample in the form of plate, 1.76 g of nitrogen dioxide and 18.1 g of liquefied carbon dioxide put in the 50 ml stainless steel autoclave were heated to 63° C., the pressure inside reached 8.6 MPa. After the mixture comprising the said substances was allowed to react at 63° C. for 1 hour, the autoclave was cooled until the pressure inside dropped back to atmospheric pressure, then removed excessive nitrogen dioxide. The obtained sample kept the form of plate, and IR absorption at 1389 and 1300 cm$^{-1}$ was confirmed. The obtained sample, after 14.9 g of liquefied carbon dioxide were admitted anew, was treated at 140° C. under 9.6 MPa for 1 hour, and was taken out of the autoclave after it was cooled and the pressure dropped down to atmospheric pressure. The thus obtained sample lost IR absorption at 1389 cm$^{-1}$ and 1300 cm$^{-1}$, and showed IR absorption at 1716 cm$^{-1}$ and 1551 cm$^{-1}$. The thus obtained sample was confirmed to come under the medium-size molecule that has carboxylic acid and nitroso group as oxidizing intermediate introduced into the carbon chains.

Example 12

When 0.2 g of isotactic polypropylene, 6.19 g of nitrogen dioxide and 9.6 g of liquefied carbon dioxide put in the 50 ml stainless steel autoclave were heated to 140° C., the pressure inside reached 9.3 MPa. After the mixture comprising the said substances was allowed to react at 140° C. for 1 hour, the autoclave was cooled until the pressure inside dropped back to atmospheric pressure, then opened to see a liquid substance formed therein. The said substance was taken out of the autoclave with use of 50 ml of chloroform, and 0.27 g of matter soluble in chloroform was obtained. The matter that was not dissolved in chloroform was dissolved in acetone, and 0.14 g of the matter soluble was obtained. The matter soluble in chloroform was found to form therein methyl succinic acid and syn-2,4-dimethyl glutaric acid and not to form anti-2,4-dimethyl glutaric acid. The matter soluble in acetone has IR absorption in the vicinity of 3000 cm$^{-1}$, and at 1715 cm$^{-1}$ and 1556 cm$^{-1}$.

Example 13

When 0.2 g of polystyrene foam sample, 1.98 g of nitrogen dioxide and 9.6 g of liquefied carbon dioxide put in the 50 ml stainless steel autoclave were heated to 140° C., the pressure inside reached 8.0 MPa. After the mixture comprising the said substances was allowed to react at 140° C. for 1 hour, the autoclave was cooled until the pressure inside dropped back to atmospheric pressure, then opened to see a substance of light yellow color formed therein. The said substance was taken out of the autoclave with use of chloroform, and separated into the matters soluble and insoluble in chloroform by means of filtration. The said soluble matter was 0.03 g in weight, and was found to form benzoic acid and 4-nitrobenzoic acid by $^1$H NMR. The matter insoluble in chloroform showed IR absorption in the vicinity of 1712 cm$^{-1}$ and 1520 cm$^{-1}$ and in the vicinity of 1350 cm$^{-1}$. The severance of polystyrene and nitrification in the benzene ring were seen.

Example 14

When 0.2 g of granular polyvinyl chloride sample, 1.83 g of nitrogen dioxide and 11.8 g of liquefied carbon dioxide put in the 50 ml stainless steel autoclave were heated to 150° C., the pressure inside reached 9.0 MPa. After the mixture comprising the said substances was allowed to react at 150° C. for 1 hour, the autoclave was cooled until the pressure inside dropped back to atmospheric pressure, then opened to see a substance of light yellow color formed therein. The said substance was separated into the matters soluble and insoluble in chloroform by means of filtration. The said soluble matter was 0.11 g in weight, and the said insoluble matter was 0.12 g. Both of those matters showed IR absorption in the vicinity of 3000 cm$^{-1}$ and at 1719 cm$^{-1}$ and 1569 cm$^{-1}$ and in the vicinity of 1350 cm$^{-1}$.

Example 15

When 1.0 g of paraffin wax sample, 3.2 g of nitrogen dioxide and 19.8 g of liquefied carbon dioxide put in the 50 ml stainless steel autoclave were heated to 130° C., the pressure inside reached 15.6 MPa. After the mixture comprising the said substances was allowed to react at 130° C. for 15 hours, the autoclave was cooled until the pressure inside dropped back to atmospheric pressure, then opened to obtain 1.47 g of a semisolid formed therein.

This crude product was confirmed by means of the said gas chromatography to contain 0.22 g of succinic acid, 0.16 g of glutaric acid, 0.07 g of adipic acid, 0.02 g of pimelic acid, 0.01 g of azelaic acid and 0.01 g of sebacic acid. Besides, the average length of the chains of resulting dicarboxylic acid was estimated to be as length as 6.0 pieces of carbon with use of the said $^1$H NMR.

What is claimed is:

1. A method for cutting polymer chains which is characterized in cutting a part or all of the molecular chains of polymer substances by nitrogen oxides in inert gas wherein said nitrogen oxides comprises at least one of the group of nitrogen dioxide and dinitrogen tetraoxide and said inert gas comprises supercritical carbon dioxide.

2. A method for cutting polymer chains according to claim 1 wherein the polymer substances are at least one of those selected from addition polymerization type, polyaddition type, condensation polymerization type, polycondensation type, or waste polymers thereof, or petroleum fractions of high boiling point.

3. A method for cutting polymer chains according to claim 2 wherein main molecular chains of the polymer substance are of carbon-to-carbon bond.

4. A method for cutting polymer chains according to claim 1 wherein the length of the molecular chains is controlled in at least one of the following manners:

(1) changing the quantities of nitrogen oxides in relation to those of the said polymer substances, (2) changing reaction temperature, (3) changing reaction pressure by means of inert gas, (4) changing reaction time, or (5) changing additives.

5. A method for cutting polymer chains according to claim 1 wherein at least one of the compounds represented by the following general formula [1], [2], [3], [4], [5], [6] or [7] is obtained, wherein the general formula [1] consists essentially of HOOCRCOOH, the general formula [2] consists essentially of HOOCRNO2, the general formula [3] consists essentially of HOOCRNO, the general formula [4] consists essentially of ONRNO, the general formula [5] consists essentially of ONRNO2, the general formula [6] consists essentially of O2NRNO2, wherein R appearing in the above formulae represents zero carbon chains, or one or more carbon chains, which may or may not have branching, may or may not be cyclized, and in addition may have an unsaturated linkage and the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group, and wherein the general formula [7] consists essentially of RCOOH, wherein R appearing in the formula [7] represents a single hydrogen atom, or one or more carbon chains, which may or may not have branching, may or may not be cyclized, and in addition may have an unsaturated linkage and where the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group.

6. A method for producing chemical raw materials which is characterized in obtaining medium-size or small-size molecules through cutting a part or all of the molecular chains of polymer substances by nitrogen oxides in inert gas wherein said nitrogen oxides comprises at least one of the group of nitrogen dioxide and dinitrogen tetraoxide and said inert gas comprises supercritical carbon dioxide.

7. A method for producing chemical raw materials according to claim 6 wherein the polymer substance is at least one of those selected from addition polymerization type, waste polymers, or petroleum fractions of high boiling point.

8. A method for producing chemical raw materials according to claim 7 wherein main molecular chains of the polymer substance are of carbon-to-carbon bond.

9. A method for producing chemical raw materials according to claim 8 wherein the length of the molecular chains is controlled in at least one of the following manners:

(1) changing the quantities of nitrogen oxides in relation to those of the said polymer substances, (2) changing reaction temperature, (3) changing reaction pressure by means of inert gas, (4) changing reaction time, and (5) changing additives.

10. A method for producing chemical raw materials according to claim 6 wherein at least one of the compounds represented by the following general formula [1], [2], [3], [4], [5], [6] or [7] is obtained wherein the general formula [1] consists essentially of HOOCRCOOH, the general formula [2] consists essentially of HOOCRNO2, the general formula [3] consists essentially of HOOCRNO, the general formula [4] consists essentially of ONRNO, the general formula [5] consists essentially of ONRNO2, the general formula [6] consists essentially of O2NRNO2, wherein R appearing in the above formulae represents zero carbon chains, or one or more carbon chains, which may or may not have branching, may or may not be cyclized, and in addition may have an unsaturated linkage and wherein the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group, and wherein the general formula [7] consists essentially of RCOOH wherein R appearing in formula [7] represents a single hydrogen atom, or one or more carbon chains, which may or may not have branching, may or may not be cyclized, and in addition may have an unsaturated linkage, and where the hydrogen atoms may be replaced by substituents comprising halogen atoms, hydroxyl group, alkoxy group, aryloxy group, acyloxy group, amino group, amide group, cyano group, nitro group, nitroso group, sulfone group, carboxyl group, alkoxy carbonyl group, aryloxy carbonyl group, formyl group, alkyl carbonyl group, aryl carbonyl group or aryl group.

* * * * *

UNITED STATES PATENT AND TRADEMARK OFFICE
CERTIFICATE OF CORRECTION

PATENT NO. : 6,841,709 B2 Page 1 of 1
APPLICATION NO. : 09/984519
DATED : January 11, 2005
INVENTOR(S) : Masaaki Yoshida It is certified that error appears in the above-identified patent and that said Letters Patent is hereby corrected as shown below:

On Title page item 76
The address of the inventor reading, "2-4-20, Izumigaka, Utsunomiya-Shi, Tochigi, 321-0952 (JP)" should read -- 2-4-20, Izumigaoka, Utsunomiya-Shi, Tochigi, 321-0952 (JP) --

Claim 5, line 11 Col. 11, Line 11 "HOOCRNOO2" should read --- $HOOCRNOO_2$ --.
Claim 5, line 14 Col. 11, Line 14 "ONRNO2" should read -- $ONRNO_2$ --.
Claim 5, line 15 Col. 11, Line 15 "O2NRNO2" should read -- $O_2NRNO_2$ --.
Claim 10, line 20 Col. 12, Line 20 "HOOCRNOO2" should read -- $HOOCRNOO_2$ --.
Claim 10, line 23 Col. 12, Line 23 "ONRNO2" should read -- $ONRNO_2$ --.
Claim 10, line 24 Col. 12, Line 24 "O2NRNO2" should read -- $O_2NRNO_2$ --.

Signed and Sealed this

Twenty-seventh Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 6,841,709 B2  Page 1 of 1
APPLICATION NO. : 09/984519
DATED : January 11, 2005
INVENTOR(S) : Masaaki Yoshida It is certified that error appears in the above-identified patent and that said Letters Patent is hereby corrected as shown below:

Column 11, "$HOOCRNOO_2$" should read -- $HOOCRNO_2$ --.
Column 12, "$HOOCRNOO_2$" should read -- $HOOCRNO_2$ --.

Signed and Sealed this

Twelfth Day of June, 2007

JON W. DUDAS
*Director of the United States Patent and Trademark Office*